United States Patent
Grow et al.

(10) Patent No.: US 8,206,929 B2
(45) Date of Patent: Jun. 26, 2012

(54) NUCLEIC ACID AMPLIFICATION WITH ALLELE-SPECIFIC SUPPRESSION OF SEQUENCE VARIANTS

(75) Inventors: Michael Grow, El Cerrito, CA (US); Victoria Brophy, Martinez, CA (US)

(73) Assignee: Roche Molecular Systems, Inc., Pleasanton, CA (US)

(*) Notice: Subject to any disclaimer, the term of this patent is extended or adjusted under 35 U.S.C. 154(b) by 277 days.

(21) Appl. No.: 12/683,111

(22) Filed: Jan. 6, 2010

(65) Prior Publication Data
US 2010/0173311 A1    Jul. 8, 2010

Related U.S. Application Data

(60) Provisional application No. 61/143,113, filed on Jan. 7, 2009.

(51) Int. Cl.
C12Q 1/68    (2006.01)
C12P 19/34   (2006.01)

(52) U.S. Cl. .................................. 435/6.12; 435/91.2
(58) Field of Classification Search ................ 435/6.12, 435/91.2
See application file for complete search history.

(56) References Cited

U.S. PATENT DOCUMENTS

| | | | |
|---|---|---|---|
| 5,849,497 A | 12/1998 | Steinman | |
| 6,001,611 A | 12/1999 | Will | |
| 6,479,242 B1 * | 11/2002 | Guo et al. | 435/6.11 |
| 2004/0053254 A1 * | 3/2004 | Wangh et al. | 435/6 |
| 2004/0115674 A1 | 6/2004 | Knott et al. | |
| 2007/0077588 A1 * | 4/2007 | Will | 435/6 |
| 2008/0176226 A1 | 7/2008 | Chiou et al. | |
| 2009/0053720 A1 | 2/2009 | Newton | |

FOREIGN PATENT DOCUMENTS

| | | |
|---|---|---|
| EP | 1253205 A1 | 10/2002 |
| WO | 0066783 A | 11/2000 |
| WO | 0066783 A3 | 11/2000 |
| WO | 2010000030 | 3/2010 |

OTHER PUBLICATIONS

Lowe et al. Nucleic acid research, 1990, vol. 18(7), p. 1757-1761.*
The nucleic acid search reports (ACA60779, ACA60780, ATC62526).*
Downward, Julian, 2003, "Targeting RAS Signalling Pathways in Cancer Therapy", Nature Reviews, 3:11-22.
Ikediobi, O. N., 2008, "Somatic Pharmacogenomics in Cancer", The Pharmacogenomics Journal, 8:305-314.
Lea, I. A., et al., 2007, "Genetic Pathways and Mutation Profiles of Human Cancers: Site-and Exposure-Specific Patterns", National Institute of Health, 28(9):1851-1858.
Pao, William, et al., 2005, "KRAS Mutations and Primary Resistance of Lung Adenocarcinomas to Gefitinib or Erlotinib", PLOS Medicine, 2(1):e17.
Yeang, Chen-Hsiang, et al., 2008, "Combinatorial Patterns of Somatic Gene Mutations in Cancer", FASEB Journal, 22:2605-2622.
Yu, Dan, et al., 1997, "Specific Inhibition of PCR by Non-Extendable Oligonucleotides Using a 5' to 3' Exonuclease-Deficient DNA Polymerase", BioTechniques, 23:714-720.
Seyama, Toshio, et al., 1992, "A novel blocker-PCR method for detection of rare mutant alleles in the presence of an excess amount of normal DNA", Nucleic Acids Research, 20(10):2493-2496.

* cited by examiner

Primary Examiner — Kenneth R. Horlick
Assistant Examiner — Joyce Tung
(74) Attorney, Agent, or Firm — Olga Kay

(57) ABSTRACT

The present invention is an improved method of selective amplification of certain variants of the target sequence, enhanced by allele-specific suppression of amplification of one or more of the other variants of the target sequence. The improvement is accomplished by providing an oligonucleotide, capable of hybridizing to the desired variant of the target sequence with the lesser affinity than to the undesired variants of the target sequence and optionally, by providing chemically modified primers and hot-start conditions.

9 Claims, 10 Drawing Sheets

5% Mutant

1% Mutant

5% Mutant

1% Mutant

5% Mutant

1% Mutant

5% Mutant

1% Mutant

FIGURE 10

Target sequence

SEQ ID NO: 1 (Wild-Type KRAS amplicon)

5'-TGACATGTTCTAATATAGTCACATTTTCATTATTTTTATTATAAGGCCTGCT
GAAAATGACTGAATATAAACTTGTGGTAGTTGGAGCTGGTGGCGTAGGCAAGAG
TGCCTTGACGATACAGCTAATTCAGAATCATTTTGTGGACGAATATGATCCAACA
ATAGAGGTAAATCTTGT-3'

SEQUENCE LISTING

```
<160> NUMBER OF SEQ ID NOS: 8

<210> SEQ ID NO 1
<211> LENGTH: 178
<212> TYPE: DNA
<213> ORGANISM: Homo sapiens

<400> SEQUENCE: 1
tgacatgttc taatatagtc acattttcat tatttttatt ataaggcctg ctgaaaatga      60
ctgaatataa acttgtggta gttggagctg gtggcgtagg caagagtgcc ttgacgatac     120
agctaattca gaatcatttt gtggacgaat atgatccaac aatagaggta aatcttgt       178

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcctgctga aaatgactga atataaactt gt                                    32

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 3
gaauuagcug uaucgucaag gcactc                                          26

<210> SEQ ID NO 4
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 4
gaauuagcug uaucgucaag gcactc                                           26

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<221> NAME/KEY: modified_base
<222> LOCATION: (8)..(8)
<223> OTHER INFORMATION: Deoxyinosine
<220> FEATURE:
<221> NAME/KEY: modified_base
<222> LOCATION: (11)..(11)
<223> OTHER INFORMATION: Deoxyinosine

<400> SEQUENCE: 5
ugccuacncc nccagcuc                                                    18

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 6
gagaaaccug ucucucuugg auauuctc                                         28

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcatgtactg gtccctcatt gcac                                             24

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 8
acuccucttg accugcu                                                     17
```

NUCLEIC ACID AMPLIFICATION WITH ALLELE-SPECIFIC SUPPRESSION OF SEQUENCE VARIANTS

SEQUENCE LISTING

The instant application contains a Sequence Listing which has been submitted via EFS-Web and is hereby incorporated by reference in its entirety. Said ASCII copy, created on Dec. 16, 2009, is named 27874US1.txt, and is 2,725 bytes in size.

FIELD OF THE INVENTION

The invention relates to the field of nucleic acid-based molecular diagnostics, and more specifically, to an improved method of amplification of nucleic acid sequences with allele-specific suppression of amplification of undesired sequence variants.

BACKGROUND OF THE INVENTION

Nucleic acid-based diagnostic tests are widely used in medicine, forensics and environmental applications. Detecting variations in a particular nucleic acid sequence provides information about polymorphisms and mutations, including disease-causing mutations. For example, detecting an individual's mutant genotype provides disease carrier status for genetic counseling. A more challenging task is detecting somatic mutations that arise in tissues and cause disease or disease progression. For example, many cancers are caused by a particular mutation. Later, additional mutations accumulate in cancer cells during tumor progression. See Lea et al. (2007) *Genetic pathways and mutation profiles of human cancers: site and exposure-specific patterns*, Carcinogenesis, 28(9):1851-1858. Downward, J. (2003) *Targeting RAS signaling pathways in cancer therapy* (2005), Nature Rev. Cancer, 3:11-22. These mutations are predictive of disease outcome and of response to therapy. See Ikediobi et al. (2008) *Somatic pharmacogenomics in cancer*, Pharmacogenomics J., 8:305-314, Pao et al. (2005) *KRAS mutations and primary resistance of lung adenocarcinomas to gefitinib and or erlotinib*, PLoS Medicine, 2(1), e17. The ability to detect such mutations is extremely useful in cancer diagnostics and treatment. However, detection of the mutations, especially early detection, faces many technical challenges.

A major challenge in detecting a cancer-related mutation is the rare nature of the mutation, especially when it first arises in a single cell during carcinogenesis. Initially, only a subpopulation of cells carries the mutation, while the surrounding cells still carry the wild-type sequence. Therefore, in a nucleic acid isolate, the newly-mutated nucleic acid is obscured by the excess of the wild-type nucleic acid. Many allele-specific detection methods (such as allele-specific PCR) involve preferential amplification of the sequence of interest (mutant sequence) over the undesired sequence (wild-type sequence). Unfortunately, in most cases, the selectivity of the assay is not perfect, i.e. the undesired sequence is also amplified, but a lot less efficiently than the desired sequence. Because the undesired (wild-type) sequence is present in great molar excess over the mutant sequence, the disadvantage is erased and the wild-type sequence is amplified predominantly, obscuring the presence of the mutant sequence.

Some methods have been developed in response to this challenge. For example, U.S. Pat. No. 5,849,497 and application Ser. No. 12/186,311, filed on Aug. 5, 2008, teach using an amplification blocker that would prevent the amplification of the competing undesired sequence. In this approach, the blocker is a non-extendible oligonucleotide which forms a stable hybrid with the undesired sequence (but not with the desired sequence) downstream of one of the amplification primers. When the blocker is stably hybridized, a DNA polymerase deficient in the 5'-3'-nuclease activity is unable to complete the extension of the primer. The success of this approach depends on the sequence divergence between the desired and the undesired sequences. The approach works best where there are multiple differences between the sequences, ensuring that the hybrid between the blocker and the sequence to be suppressed is stable, while the hybrid between the blocker and the sequence to be amplified is unstable.

The above method has several technical limitations. A longer blocker oligonucleotide is more efficient at blocking, but may be unable to discriminate, thus blocking amplification of all sequence variants. A shorter blocker may be unable to block any amplification efficiently. In some sequence contexts, there may be so few differences that a blocker is capable of very weak discrimination. Therefore, in some loci of clinical interest, the blocker alone is insufficient to solve the technical problems of allele-specific amplification.

SUMMARY OF THE INVENTION

The present invention is an improved method of selective amplification of a desired variant of a target sequence, for which said target sequence exists in the form of more than one variant, the method comprising the steps of: providing a sample possibly comprising at least one variant of the target sequence in a reaction mixture; providing a first oligonucleotide, capable of hybridizing to more than one variant of the target sequence; providing a second oligonucleotide, capable of hybridizing to more than one variant of the target sequence, wherein at least a fraction of said second oligonucleotide contains a modified base in one or more nucleotides at or near the 3'-terminus; providing a third oligonucleotide, capable of hybridizing to the desired variant of the target sequence with the lesser affinity than to the undesired variants of the target sequence and designed to hybridize to the same strand and between 0 and 60 nucleotides downstream of said second oligonucleotide; providing a nucleic acid polymerase substantially lacking 5'-3' nuclease activity and possessing a hot-start capability; subjecting said reaction mixture to polymerase chain reaction, wherein said third oligonucleotide substantially inhibits extension of said second oligonucleotide by said nucleic acid polymerase when said third oligonucleotide is hybridized to the undesired variant of the target sequence, but does not substantially inhibit extension of said second oligonucleotide by said nucleic acid polymerase when said third oligonucleotide is hybridized to the desired variant of the target sequence.

BRIEF DESCRIPTION OF THE DRAWINGS

FIG. 10 shows the target nucleic acid sequence used in the examples of the present invention.

DETAILED DESCRIPTION OF THE INVENTION

Figure 1:
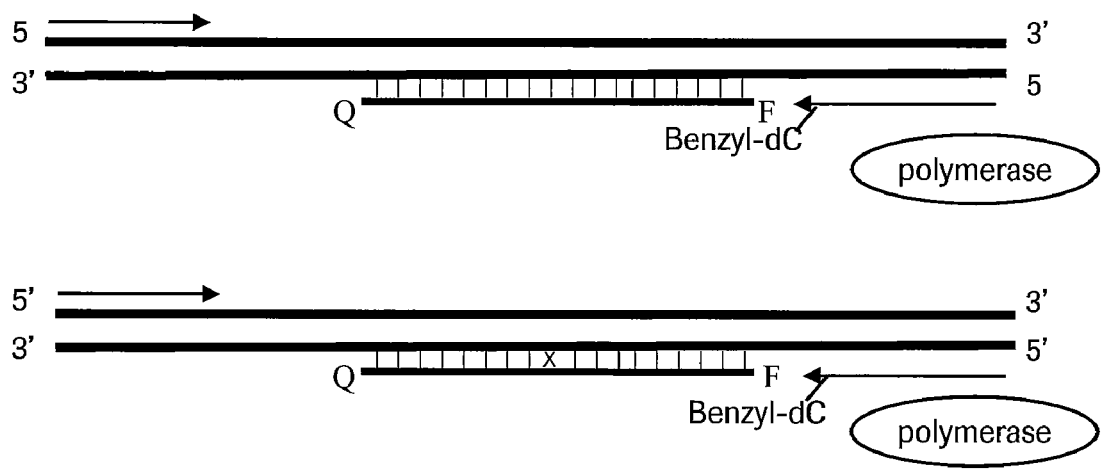
FIG. 1 is a schematic representation of the method of the present invention.

The present invention is an improved method of selective amplification of certain variants of the target sequence, enhanced by allele-specific suppression of amplification of one or more of the other variants of the target sequence.

DEFINITIONS

Unless defined otherwise, all technical and scientific terms used herein have the same meaning as commonly understood by one of ordinary skill in the art to which this invention pertains. In describing and claiming the present invention, the following definitions will be used.

A "biological sample" or "sample" refers to any substance possibly containing a nucleic acid of interest. The sample can be obtained by any means known to those of skill in the art. Such sample can be an amount of tissue or fluid, or a purified fraction thereof, isolated from a human or other animal, including, but not limited to: body fluid, such as plasma, serum, spinal fluid, saliva, peritoneal fluid, lymphatic fluid, aqueous or vitreous humor, synovial fluid, urine, tears, seminal fluid, vaginal fluids, pulmonary effusion, serosal fluid; tissue, including blood, normal tissues, tumors and paraffin embedded tissues. Samples also can also be (or be derived from) in vitro cell cultures. The samples can include conditioned medium, cells and cell components. The nucleic acid can be obtained from a biological sample by procedures well known in the art.

A "blocker oligonucleotide" as used herein refers to an oligonucleotide that:

(1) forms a duplex with some variants of the target sequence at a sufficiently low melting temperature to allow for a polymerase significantly lacking 5'-3' nuclease activity to displace the blocker oligonucleotide and to replicate those variants of the target sequence; and (2) forms a duplex with other variants of the target sequence, at a sufficiently high melting temperature to impair a polymerase significantly lacking 5'-3' nuclease activity from replicating those variants of the target sequence.

The blocker oligonucleotide typically includes a modification at the 3' end to prevent extension of the blocker oligonucleotide by a polymerase.

A "target sequence" refers to a nucleotide sequence to be detected in a biological sample. The target sequence can be a portion of a larger sequence or an isolated nucleic acid.

The phrase "impair amplification" refers to eliminating or measurably (detectably) reducing amplification of a sequence. As described herein, a blocker oligonucleotide can impair amplification of one or more variants of the target sequence, so that the amplification of such variants is undetectable, or is less detectable, compared to a control reaction lacking the blocker oligonucleotide.

The terms "nucleic acid" and "polynucleotide" are used interchangeably, and refer to a polymer of RNA, DNA, as well as modified forms thereof such as peptide nucleic acids (PNA), locked nucleic acids (LNA), and the like. There is no intended distinction in length between the term "nucleic acid" and "polynucleotide." An "oligonucleotide" is a generally shorter nucleic acid, which is commonly single-stranded.

A nucleic acid is either single-stranded or double-stranded and will generally contain phosphodiester bonds, although in some cases, nucleic acid analogs are included that may have alternate backbones, including, for example, phosphoramide (Beaucage et al. (1993) *Tetrahedron* 49(10): 1925; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644, 048), phosphorodithioate (Briu et al. (1989) *J. Am. Chem. Soc.* 111:2321), O-methylphosphoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207). Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, *ASC Symposium Series* 580, Carbohydrate Modifications in Antisense Research, Ed. Y. S. Sanghvi and P. Dan Cook. Nucleic acids containing one or more carbocyclic sugars are also included within the definition of nucleic acids (Jenkins et al. (1995) *Chem. Soc. Rev.* pp 169-176). Several nucleic acid analogs are also described in, e.g., Rawls, *C & E News* Jun. 2, 1997 page 35. These modifications of the ribose-phosphate backbone may be done to facilitate the addition of additional moieties such as labeling moieties, or to alter the stability and half-life of such molecules in physiological environments.

Nucleic acids generally contain the typical nitrogenous bases (adenine, guanine cytosine, thymine and uracil). However, nucleic acids may also contain non-naturally occurring heterocyclic or other modified bases. In particular, such bases are described in Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640. Other bases include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303. Yet other representative heterocyclic bases include hypoxanthine, inosine, xanthine, 8-aza derivatives of 2-aminopurine, 2,6-diaminopurine, 2-amino-6-chloropurine, hypoxanthine, 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, 4-acetylcytidine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenosine, 1-methylguanosine, 1-methylinosine, 2,2-dimethylguanosine, 7-deazaadenosine, 2-methyladenosine, 2-methylguanosine, 3-methylcytidine, 5-methylcytidine, N6-methyladenosine, 7-methylguanosine, 7-deazaguanosine, 5-methylaminomethyluracil, 5-methoxyaminomethyl-2-thiouracil, beta-D mannosylqueosine, 5'-methoxycarboxymethyluracil, 5-methoxyuracil, 2-methylthio-N-6-isopentenyladenosine, uracil-5-oxyacetic acid (v), wybutoxosine, pseudouracil, queosine, 2-thiocytidine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine, and the like.

Additional examples of non-naturally occurring bases and nucleotides are 5-propynyl pyrimidines, described in U.S. Pat. No. 5,484,908; and other modified pyrimidines described in U.S. Pat. Nos. 5,645,985 and 5,830,653. [2.2.1] bicyclo nucleotides are described in U.S. Pat. No. 6,639,059. Other modified purines and pyrimidines were described in U.S. Pat. No. 6,011,611.

A term "primer extension" refers to the ability of a nucleotide incorporating biocatalyst, such as a polymerase, to add one or more nucleotides to the 3' terminus of a primer.

"Conditions suitable for primer extension" refer to conditions under which primers that hybridize to a template nucleic acid are extended by a nucleotide-incorporating biocatalyst, such as a polymerase. For example, such conditions occur during a polymerase chain reaction (PCR) annealing and extension step. Those of skill in the art will appreciate that such conditions can vary, and are generally influenced by ionic strength of the solution, temperature and sequence of the particular template nucleic acid and primers. Various PCR conditions are described in *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., 1990 Academic Press, N.Y.).

A nucleic acid is "complementary" in relation to another nucleic acid when at least a subsequence of the nucleic acid can combine in an antiparallel association with at least a subsequence of the other nucleic acid to form a duplex. In the context of the present invention, in an oligonucleotide that is "fully complementary" to a particular nucleic acid sequence, each base of the oligonucleotide is complementary to the corresponding base in the particular sequence. An oligonucleotide is "partially complementary" to a particular nucleic acid sequence when one or more of the bases in the oligonucleotide are not complementary ("mismatched") with the corresponding bases in the other nucleic acid. Modified bases are generally considered to be complementary to the same base as their non-modified precursors. For example, 7-deazaguanine is considered to be complementary to cytosine and N6-benzyl-adenine is considered to be complementary to thymine.

A "primer nucleic acid" or "primer" is an oligonucleotide that can hybridize to a target nucleic acid (sometimes called template nucleic acid) and permit chain extension or elongation by a nucleotide incorporating biocatalyst, such as a polymerase, under appropriate reaction conditions. A primer nucleic acid is typically a natural or synthetic oligonucleotide, ranging from about 6 to about 100 nucleotides in length, although most commonly primers are between 15 and 35 nucleotides in length. Short primer nucleic acids generally require lower temperatures to form sufficiently stable hybrid complexes with template nucleic acids. A primer that is at least partially complementary to the template nucleic acid is typically sufficient for extension to occur. The design of suitable primers for the amplification of a given target sequence is well known in the art and described in the literature cited herein. A primer can be labeled, if desired, by incorporating a label detectable by spectroscopic, photochemical, biochemical, immunochemical, chemical or other techniques. To illustrate, useful labels include; radioisotopes, fluorescent dyes, electron-dense reagents, enzymes (as commonly used in ELISA), haptens, and proteins for which antisera or monoclonal antibodies are available. Many of these and other labels are described herein or are otherwise known in the art.

As used herein, the term "probe" refers to an oligonucleotide (or other nucleic acid sequence) which, under suitable conditions, can form a duplex structure with a region of a target nucleic acid, due to partial or complete complementarity with at least a sub-sequence in the target nucleic acid. As discussed herein, the probe is typically labeled to allow detection of the target nucleic acid. The 3'-terminus of the probe is typically designed to prevent extension of the probe by a nucleotide incorporating biocatalyst. This can be achieved by using non-complementary bases or by adding a chemical moiety, such as biotin or a phosphate group, to the 3'-hydroxyl group of the 3'-terminal nucleotide. These chemical moieties at the 3'-end can serve a dual purpose by also acting as a label for subsequent detection or capture of the nucleic acid to which the probe has hybridized. Prohibiting extension can also be achieved by removing the 3'-OH or by using a nucleotide that lacks a 3'-OH such as a dideoxynucleotide, or by adding a bulky group that blocks extension by steric hindrance. As discussed further herein, the blocker oligonucleotides of the invention can optionally function as probes.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

The terms "nucleic acid polymerase substantially lacking the 5'-3' nuclease activity" or "5'-3'-nuclease-deficient enzyme", or for simplicity, "nuclease-deficient enzyme" refer to a polymerase that has 50% or less of the 5'-3' activity than Taq DNA polymerase. The methods of measuring the 5'-3' nuclease activity and conditions for measurement have been described in U.S. Pat. No. 5,466,591. The examples of polymerases lacking the 5'-3' nuclease activity include the Stoffel fragment of Taq DNA polymerase (U.S. Pat. No. 5,466,591), mutants of *Thermus africanus* DNA polymerase (U.S. Pat. No. 5,968,799), mutants of *Thermotoga maritima* DNA polymerase (U.S. Pat. Nos. 5,624,833 and 5,420,029), mutants of *Thermus* species sps17 and *Thermus* species Z05 DNA polymerases (U.S. Pat. Nos. 5,466,591 and 5,405,774). 5'-3' nuclease deficient enzymes may also be chimeras, i.e. chimeric proteins, composed of domains derived from more than one species and having mutations that eliminate the 5'-3' nuclease activity (U.S. Pat. Nos. 5,795,762 and 6,228,628).

Exemplary thermostable DNA polymerases include those from *Thermus thermophilus, Thermus caldophilus, Thermus* sp. Z05 (see, e.g., U.S. Pat. No. 5,674,738), *Thermus aquaticus, Thermus flavus, Thermus filiformis, Thermus* sp. sps17, *Deinococcus radiodurans, Hot Spring family B/clone 7, Bacillus stearothermophilus, Bacillus caldotenax, Escherichia coli, Thermotoga maritima, Thermotoga neapolitana* and *Thermosipho africanus*. The full nucleic acid and amino acid sequences for numerous thermostable DNA polymerases are available in the public databases.

As used herein, the term "$T_m$" refers to the "melting temperature." The melting temperature is the temperature at which one half of a population of double-stranded nucleic acid molecules (i.e. nucleic acid duplexes that are completely or partially complementary), become dissociated into single strands. The prediction of a $T_m$ of a duplex polynucleotide takes into account the base sequence as well as other factors, including structural and sequence characteristics, the degree of complementarity, the nature of the oligomeric linkages and the ionic strength of the solution. Methods for predicting and experimentally determining $T_m$ are known in the art. For example, $T_m$ is traditionally determined by a melting curve analysis, wherein a duplex nucleic acid molecule is gradually heated and the state of association/dissociation of the duplex is monitored by measuring a change in a detectable parameter that correlates with the melting of the duplex. The change in the parameter is plotted against the change in temperature. The $T_m$ is determined from this melting curve.

A term "hot start" in the context of a nucleic acid amplification reaction is a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol.

The present invention is an improvement of the selective amplification of nucleic acids, which uses allele-specific suppression of amplification of the undesired variants of the target sequence. A schematic diagram of the method of the present invention is shown on FIG. 1. The diagram shows a double-stranded nucleic acid target and a blocker oligonucleotide, capable of annealing to the target downstream of one of the primers (arrows). The 3'-terminus of the primer positioned upstream of the blocker is chemically modified. F represents a fluorescent reporter moiety and Q represents a fluorescence quencher, conjugated to the blocker oligonucleotide.

The improvement of the present invention is based on the discovery that the relative proximity of the primer and the blocker oligonucleotide, as well as certain chemical modifications of the primer and the polymerase, greatly improve selective amplification.

The general method of suppressing amplification of the undesired variants of the target sequence is taught in the U.S. application Ser. No. 12/186,311, filed on Aug. 5, 2008 and incorporated herein by reference. The success of the allele-specific suppression of amplification by the blocker oligonucleotide depends on the stability of the hybrid between the blocker oligonucleotide and the target. When the hybrid with the blocker is more stable (as in the case of the undesirable sequences), amplification is suppressed by the blocker. When the hybrid with the blocker is less stable (as in the case of the sequence to be amplified), amplification takes place. A traditional way of increasing the stability of a nucleic acid hybrid is to increase the length of the hybridizing nucleic acids. However, increased length of the blocker oligonucleotide will impair discrimination. The amplification of all variants of the target sequence will become suppressed. Therefore, for any given target sequence, the ability to optimize the blocker oligonucleotide is limited.

As described in the application Ser. No. 12/186,311, the blocker oligonucleotide is typically designed to hybridize anywhere between the two primer oligonucleotides. The blocker or blockers can hybridize to one or both strands of the target nucleic acid. The only known requirement was that the blocker must hybridize downstream of and to the same strand as the primer whose extension is to be suppressed. However, in the context of the present invention, it was discovered that the distance between the 3'-end of the primer and the 5'-end of the blocker oligonucleotide affects the efficiency of blocking. Generally, the optimal distance between the respective ends of the primer and blocker is between 0 and 60 nucleotides. For each particular target sequence, the optimal distance within that range may be determined empirically, using the guidance provided herein.

Another innovation discovered herein is that the 3'-end of the primer, positioned upstream of the blocker oligonucleotide and hybridizing to the same strand, can be chemically modified to improve the degree of blocking. Traditionally, chemical modifications are found in allele-specific primers, i.e. primers that match a desired sequence variant but have mismatches with the undesired sequence variants. The examples of chemical modifications that affect the specificity of amplification primers are described in the U.S. Pat. No. 6,011,611, incorporated herein by reference. These modifications include covalent attachments at the exocyclic amino groups of certain nitrogenous bases. The modifications, occurring in one or more nucleotides located within about five 3'-terminal nucleotides of the primer, are generally known to increase the specificity of amplification. According to the prior art, the chemical modification of the primer is not necessary when the primer is equally complementary to the desired and the undesired sequence variants.

Surprisingly, it was found by the present inventors that the chemical modification of the primer plays a role in the success of the allele-specific suppression of amplification by the blocker oligonucleotide. The effect is especially surprising because the primers themselves are not allele-specific as the prior art would require. The primers are equally complementary to both the desired and the undesired sequence variants.

In some embodiments, the present invention is a selective amplification assay with allele-specific suppression of the amplification of the undesired sequence variant, which is conducted in the presence of a small amount of the desired sequence variant and a molar excess of the undesired sequence variant. In some embodiments, the ratio of the desired to the undesired sequence variant is 1:1, 1:20, 1:100, 1:1000 or higher.

The blocker oligonucleotide of the present invention is designed to anneal and hybridize to the portion of the target sequence located between the primer-binding sites. The blocker or blockers can be designed to hybridize to one or both strands of the target nucleic acid. The blocker oligonucleotide is designed to form a hybrid with a higher melting temperature with the undesired versions of the target sequence than with the desired version. The design of the blocker oligonucleotide for the suppression of amplification of the undesired sequence variants has been described in the U.S. application Ser. No. 12/186,311, filed on Aug. 5, 2008, which is incorporated herein by reference.

Generally, the blocker is designed to incorporate one or more mismatches with the desired variant of the target sequence. With the other variants of the target sequence, the blocker has fewer mismatches or none at all. Because the degree of complementarity affects the melting temperature of the nucleic acid hybrid, the $T_m$ of the hybrid formed between the blocker oligonucleotide and the desired variant of the target sequence would preferably be the lowest among all the hybrids formed by the blocker oligonucleotide. In addition to the degree of complementarity, the melting temperature of the oligonucleotide is also affected by the presence and number of the unconventional bases, which can be "stabilizing" (e.g. 5-methyl cytosine and propynyl uridine) or "destabilizing" (e.g. $N^6$-benzyl adenosine) as is known in the art. Optionally, such bases may be incorporated into the blocker oligonucleotide to further modulate its melting temperature.

Generally, the prior art teaches that the blocker oligonucleotide must be positioned between the two amplification primers and hybridize downstream of and to the same strand as the primer whose extension is to be suppressed. In the scope of the present invention, it was discovered that the relative position of the blocker and the primer oligonucleotides greatly affects the ability of the blocker to suppress amplification. For example, the blocker may be positioned 0 to 60, for example 0, 1, 2, 3 or more nucleotides downstream of the 3'-end of one of the primers, and hybridize to the same strand as that upstream primer.

The blocker oligonucleotide may be designed "manually" or using any one of the oligo design software programs known to the practitioners of the art, including Visual OMP (DNA Software, Inc., Ann Arbor, Mich.), Oligo 6 (Stratagene, La Jolla, Calif.), Sequencher (Gene Codes, Ann Arbor, Mich.) and DNAStar (DNAStar, Inc., Madison, Wis.) The goal of the design process is to create a blocker oligonucleotide with different thermodynamic stability of the hybrids between the different variants of target sequence and the blocker under the temperatures and conditions of a particular amplification assay.

In some embodiments, the blocker oligonucleotide has a dual function as a probe for the detection of amplification of the target sequence. To be used as a probe, the blocker oligonucleotide may be labeled with any type of a detectable label known in the art. For example, the label may be fluorescent, chemiluminescent, radioactive, enzymatic, etc. Such a blocker-probe oligonucleotide may be used in any number of detection methods, such as amplification detection ("growth curve") as well as a post-amplification melting assay.

In an amplification reaction according to the present invention, one or more blocker oligonucleotides can be used. The blocker oligonucleotides may be designed to hybridize to one strand of the nucleic acid to be amplified, or separate blockers may be designed to hybridize to both strands. In case more than one oligonucleotide is designed to hybridize to the same strand of the nucleic acid, the oligonucleotides may be used in the same or different rounds of the amplification reaction. For example, where the second round of amplification involves a primer positioned internally to the primer used in the first round, a blocker positioned internally to such second-round primer may be used in the second or subsequent rounds of amplification. All or at least one of the blocker oligonucleotides should be designed according to the guidelines of the present invention.

The amplification primers of the present invention are oligonucleotides at least partially complementary to at least one of the existing variants of the target sequence. The length of the primer may range between 6 and 100 nucleotides, although most primers typically range between 15 and 35 nucleotides. The methods of optimizing the primers for nucleic acid amplification have been described; for example, in *PCR Protocols: A Guide to Methods and Applications*, Innis et al., eds., (1990) Academic Press. Typically, primers are synthetic oligonucleotides, composed of A, C, G and T nucleotides. However, unconventional base nucleotides, not normally found in nucleic acids, can also be used. For example, certain modified bases are known to increase specificity of amplification, see U.S. Pat. No. 6,001,011. These modifications include alkyl, aryl or alkyl-aryl groups covalently linked to an exocyclic amino group of the nucleobase. The traditional use of these modified bases in amplification primers is to reduce non-specific amplification. However, in one aspect of the present invention, it was found that the nucleotides with bases covalently modified at the exocyclic amino groups also increase the degree of suppression of amplification using the blocker oligonucleotide.

Various nucleotide incorporating biocatalysts, such as DNA polymerases, are known in the art. Any thermostable polymerase lacking the 5'-3' nuclease activity may be used in the present invention. It is sometimes desirable to use an enzyme without the proof-reading (3'-5'-exonuclease) activity.

One example of a suitable enzyme is ΔZ05 polymerase. It may sometimes be desirable to have an enzyme with a "hot start" capability, such as the reversibly modified enzymes described in U.S. Pat. Nos. 5,677,152 and 5,773,528. One example of a hot-start enzyme is ΔZ05-Gold polymerase.

Detection of the amplification products according to the present invention may be accomplished by any method known in the art. These detection methods include the use of labeled primers and probes as well as various nucleic acid-binding dyes. The means of detection may be specific to one variant of the target sequence, or may be generic to all variants of the target sequence or even to all double stranded DNA. The non-specific detection methods may be used where the amplification of the undesired variants of the target is minimal and expected to fall below the detection limit of the method.

The amplification products may be detected after the amplification has been completed, for example, by gel electrophoresis of the unlabeled products and staining of the gel with a nucleic acid-binding dye. Alternatively, the amplification products may carry a radioactive or a chemical label, either by virtue of incorporation during synthesis or by virtue of having a labeled primer. After or during electrophoresis, the labeled amplification products may be detected with suitable radiological or chemical tools known in the art. After electrophoresis, the product may also be detected with a target-specific probe labeled by any one of the methods known in the art. The labeled probe may also be applied to the target without electrophoresis, i.e. in a "dot blot" assay or the like.

In other embodiments, the presence of the amplification product may be detected in a homogeneous assay, i.e. an assay where the nascent product is detected during the cycles of amplification, and no post-amplification handling is required. A homogeneous amplification assay using a nuclease probe has been described for example, in U.S. Pat. No. 5,210,015. Homogeneous amplification assay using nucleic acid-intercalating dyes has been described for example, in U.S. Pat. Nos. 5,871,908 and 6,569,627. The homogeneous assay may also employ fluorescent probe or probes labeled with two interacting fluorophores. The examples of such probes include "molecular beacon" probes (Tyagi et al., (1996) *Nat. Biotechnol.*, 14:303-308) or fluorescently labeled nuclease probes (Livak et al., (1995) *PCR Meth. Appl.*, 4:357-362).

Yet another embodiment of the present invention is a method where the amplification products are detected and identified by determining their unique melting temperatures ($T_m$). In one variation of the melt assay, melting of an entire amplicon is monitored using a fluorescent compound that specifically binds duplex nucleic acids. Specifically, measuring the temperature-dependent change in fluorescence of the duplex-intercalating dyes has been described in U.S. Pat. No. 5,871,908. The decrease in fluorescence reflects the melting of the amplicon, allowing one to determine the $T_m$ of the amplicon.

In another embodiment of the present invention, the hybrid is formed between target DNA and one or more fluorescently labeled probes. Typically, the probes are labeled with at least two fluorophore moieties, forming a FRET pair. In some embodiments, one of the moieties forming the FRET pair is a non-fluorescent quencher. The moieties forming the FRET pair may be conjugated to the same or separate probe molecules. The change in temperature that results in melting or formation of the template-probe hybrid is accompanied by a measurable change in fluorescence, due to the change in physical distance between the members of the FRET pair. Measuring the temperature-dependent change in fluorescence of a dye or dyes conjugated to a pair of probes or to a single probe has been described in the U.S. Pat. No. 6,174, 670. Identification of a particular genotype by its unique $T_m$ with a pair of labeled probes has been described in De Silva et al., (1998) "Rapid genotyping and quantification on the LightCycler™ with hybridization probes," *Biochemica*, 2:12-15.

In some embodiments, the present invention involves asymmetric PCR. In an asymmetric PCR mixture, one of the amplification primers is present in greater amount than the other primer. The primers are referred to as "excess primer" and "limiting primer" respectively. The nucleic acid strands resulting from the extension of these primers are referred to as "excess strand" and "limiting strand" respectively. The ratio of the excess primer to the limiting primer can be selectively manipulated and be between 200:1 and 2:1, but typically about 9:1 to 5:1. Due to an excess of the primer, the excess strand accumulates in a linear fashion in single-stranded form. This excess single strand is useful for certain post-PCR analysis methods.

In some embodiments, the present invention involves asymmetric PCR, followed by a post-PCR characterization of the amplicons via melting temperature analysis. Asymmetric PCR followed by a $T_m$ analysis has been described in a U.S. Application Publication No. 2007/0072211, incorporated herein by reference. In a typical reaction, the asymmetric PCR is conducted in the presence of one or more labeled probes. The melting and annealing of the probes is associated with a measurable change in fluorescence, which is reflective of the formation or melting of the nucleic acid duplex. Typically, in the context of asymmetric PCR, the melt probes are designed to hybridize to the "excess strand," i.e. the amplicon strand that results from the extension of the excess primer, and accumulates in a single-stranded form.

The design of hybridization probes is known in the art. Whether the probe is to serve as a nuclease probe, a single hybridization probe or a member of a pair of hybridization probes, the design of the probe oligonucleotide is guided by the same principles, known in the art and described herein and applied either manually or with a help of software.

In some embodiments of the present invention, the blocker oligonucleotide, binding adjacently to one of the primers in order to suppress amplification of the undesired variant of the sequence, may also serve as a hybridization probe or a melt probe or both. One of skill in the art would immediately recognize the design criteria applicable to such dual-function oligonucleotides. Specifically, the oligonucleotide should have a different hybrid melting temperature with different variants of the target sequence, but each of the melting temperatures should fall within the range detectable in a particular system. In most cases, this would involve melting temperatures that are measurably distinct, yet relatively close. In other embodiments of the invention, the probe or probes are oligonucleotides separate from the blocker oligonucleotide.

The probe oligonucleotides can be labeled by incorporating moieties detectable by various methods, including radiological, spectroscopic, photochemical, biochemical, immunochemical or chemical. For the fluorescence based detection, the labels can include dyes, for example of the fluorescein family (FAM, HEX, TET, JOE, NAN and ZOE), rhodamine family (Texas Red, ROX, R110, R6G and TAMRA), cyanine family (Cy2, Cy3, Cy5 and Cy7) coumarin family, oxazine family, thiazine family, squaranine family and other families of fluorescent dyes suitable for the labeling and detection of nucleic acids. In addition, a fluorescent dye may be paired with a non-fluorescent quencher moiety, exemplified by Black Hole Quenchers™ (Biosearch Tech., Novato, Calif.), Eclipse Dark Quenchers™ (Epoch Biosciences, Bothell, Wash.) and Iowa Black (Integrated DNA Tech., Coralville, Iowa).

In some embodiments, the present invention involves detection of disease-related mutations, including cancer-related mutations in the presence of the wild-type, i.e. non-mutated nucleic acid sequences. It is generally known that during cancer progression, the tumor cells accumulate mutations that confer selective advantages to the mutant cells. See Downward, J. (2003) *Targeting RAS signaling pathways in cancer therapy* (2005), Nature Rev. Cancer, 3:11-22. Often the mutations confer resistance to anti-tumor agents used in therapy. See Pao et al. (2005) *KRAS mutations and primary resistance of lung adenocarcinomas to gefitinib and or erlotinib*, PLoS Medicine, 2(1), e17. Detecting such mutations will spare the patients the trouble and unnecessary risk associated with taking an ineffective drug with unpleasant side effects. More broadly, detecting the cancer-related mutations is informative for prognosis of the existing disease, as well as for initial cancer screening.

In one embodiment, the present invention may be applied to detection of somatic mutations that arise in a subpopulation of cells. To successfully amplify and detect the mutant nucleic acid sequence, the amplification primers may be designed to hybridize to the sequences flanking the suspected mutation site. To suppress the amplification of the wild-type sequence, a blocker oligonucleotide may be designed to be perfectly (or nearly perfectly) complementary to the wild-type sequence but have one or more mismatches with the mutant sequence. The design of the blocker oligonucleotide must assure that it forms a stable hybrid with the wild-type sequence but forms an unstable (or significantly less stable) hybrid with the mutant sequence under the conditions where annealing and extension of the specific primers is to take place. For example, using the available tools of oligonucleotide design, one would be able to design a blocker oligonucleotide, such that under the typical conditions of an amplification reaction, the melting temperature of the hybrid formed by the blocker and the wild-type sequence would be higher than the annealing temperature used during thermocycling. At the same time, the melting temperature of the hybrid formed by the blocker and the mutant sequence would be lower than the annealing temperature used during thermocycling.

The oligonucleotide primers, according to the present invention, may be designed to flank any number of the suspected mutation sites of interest for a particular disease or condition, such as for example, mutations listed in Downward, J. (2003), supra. The nucleic acid sample, according to the present invention, may be obtained from fresh or preserved patient tissues and non-diseased control tissues, including the formalin-fixed paraffin-embedded tissues (FFPET).

As an illustration only and not to limit the scope of the invention, the method was applied to detect mutations in the KRAS gene, known to be associated with many human solid tumors. KRAS mutations have been found in 20-30% of non-small cell lung cancer, 30-40% of colorectal cancer and up to 90% of pancreatic cancer, Yeang et al., (2008) *Combi-* natorial pattern of somatic gene mutations in cancer, FASEB J, 22:2605-2622. KRAS mutations confer resistance to the drugs that target the Epidermal Growth Factor Receptor (EGFR). The resistance seems to apply to the EGFR-targeting drugs regardless of the mechanism of action: both tyrosine kinase inhibitors and anti-EGFR antibodies lose their effectiveness against the KRAS-mutant cells.

The KRAS gene is an especially suitable target for a mutation detection assay: about 99% of all mutations occur in only three codons: codon 12 (88%), codon 13 (10%) and codon 61 (1-3%). Such clustering of mutations allows the design of a small number of allele-specific primers or probes that would cover the entire spectrum of clinically relevant mutations.

In another aspect, the invention provides a reaction mixture for selective amplification of nucleic acids with allele-specific suppression of amplification of the undesired sequence variants. The reaction mixture comprises a first and a second oligonucleotide, capable of hybridizing to more than one variant of the target sequence, wherein at least a fraction of the second oligonucleotide contains a modified base in one or more nucleotides at or near the 3'-terminus; a third oligonucleotide, capable of hybridizing to the desired variant of the target sequence with the lesser affinity than to the undesired variants of the target sequence and designed to hybridize between 0 and 60 nucleotides downstream of said second oligonucleotide; a nucleic acid polymerase substantially lacking the 5'-3' nuclease activity and having a hot-start capability; and optionally, a target nucleic acid known to exist in more than one sequence variant. In some embodiments, the reaction mixture further comprises the reagents and solutions generally necessary for the amplification and optionally, detection of nucleic acids, including nucleic acid precursors; i.e. nucleoside triphosphates, and organic and inorganic ions, suitable for the support of the activity of the polymerase, and optionally, a detectable label. In some embodiments, the amounts of the first and second oligonucleotides in the mixture are unequal, such that the first oligonucleotide is present in excess. In some embodiments, said third oligonucleotide is labeled. In some embodiments of the invention, the target nucleic acid comprises all or portion of the KRAS gene sequence. In some embodiments, the target sequence includes one or more of the KRAS codons 12, 13 and 61.

In another aspect, the invention provides kits for conducting selective amplification of nucleic acids with allele-specific suppression of amplification of the undesired sequence variants. The kit generally includes assay-specific components as well as components generally required for performing nucleic acid amplification assays. As the assay-specific components, the kit of the present invention typically includes first and second oligonucleotides, capable of hybridizing to more than one variant of the target sequence, wherein at least a fraction of the second oligonucleotide contains a modified base in one or more nucleotides at or near the 3'-terminus; a third oligonucleotide, capable of hybridizing to the desired variant of the target sequence with the lesser affinity than to the undesired variants of the target sequence and designed to hybridize between 0 and 60 nucleotides downstream of said second oligonucleotide; a nucleic acid polymerase substantially lacking the 5'-3' nuclease activity and having a hot-start capability; and optionally, a control nucleic acid sequence comprising an amount of at least one version of the target sequence. In some embodiments, more than one version of the control nucleic acid sequence may be enclosed. In some embodiments, said third oligonucleotide is labeled. As the components generally required for nucleic acid amplification and optionally, detection, the kit of the present invention typically includes one or more of nucleic acid precursors, such as nucleoside triphosphates (deoxyribonucleoside triphosphates or ribonucleoside triphosphates), optionally, a pyrophosphatase, for minimizing pyrophosphorolysis of nucleic acids, a uracil N-glycosylase (UNG) for protection against carry-over contamination of amplification reactions, pre-made reagents and buffers necessary for the amplification reaction and optionally, detection, and a set of instructions for conducting allele-specific amplification of the present invention.

EXAMPLES

The examples below utilize a fragment of the KRAS gene, exon 2 (SEQ ID NO: 1), FIG. 10, as the target sequence. The mutant sequences contain various missense mutations at either codon 12 or codon 13 of exon 2. Codons 12 and 13 are the underlined bases in SEQ ID NO: 1 shown on FIG. 10. The probe (SEQ ID NO: 5) is perfectly matched to the wild type sequence. The mutant sequences have one or more mismatches with the probe. In the examples below, the same probe (SEQ. ID. NO: 5) is used as both amplification detection probe and a melt probe. Further, the probe serves as a suppressor of amplification of the wild-type sequence. The exon 3 sequences were co-amplified in the same reaction with the KRAS exon 2 sequences using the upstream primer SEQ ID NO. 6, downstream primer SEQ ID NO. 7 and detection probe SEQ ID NO. 8. For simplicity, the results of amplification of exon 3 sequences, detected in a separate wavelength channel, are not shown. The primer and probe sequences are shown in Table 1.

TABLE 1

| KRAS primer and probe sequences | |
|---|---|
| | Sequence (5'-3') |
| Exon 2 upstream primer | |
| SEQ ID NO: 2 | GGCCTGCTGAAAATGACTGAATATAAACTTGT |
| Exon 2 downstream primers | |
| SEQ ID NO: 3 | GAAUUAGEUGUAUEGUEAAGGEACTC |
| SEQ ID NO: 4 | GAAUUAGEUGUAUEGUEAAGGEACTM |
| Exon 2 probe | |
| SEQ ID NO: 5 | FUGEEUAEIEEIEEAGEUEQp |
| Exon 3 upstream primer | |
| SEQ ID NO: 6 | GAGAAAEEUGUEUEUEUUGGAUAUUCTC |
| Exon 3 downstream primer | |
| SEQ ID NO: 7 | TCATGTACTGGTCCCTCATTGCAM |
| Exon 3 probe | |
| SEQ ID NO: 8 | LAEUEEUCTTGACEUGEUQp |

E = 5-methyl dC
U = 5-propynyl dU
M = N⁴-benzyl dC
I = dI (deoxyinosine)
F = cx-FAM donor fluorophore (Fluorescein)
Q = BHQ-2 Black Hole ™ quencher
L = cx-HEX donor fluorophore (HEX-dye)
p = 3' phosphate

Example 1

Amplification and Melting Analysis of a Wild-Type and a KRAS-Mutant Target Separately Each 50 µl reaction contained $10^4$ copies of either wild-type or mutant target sequence, 0.7 µM exon 2 upstream (excess) primer (SEQ ID NO: 2), 0.025 µM of the first exon 2 downstream (limiting) primer (SEQ ID NO: 3), without the chemical modification) and 0.075 µM of the second exon 2 downstream (limiting) primer (SEQ. ID NO: 4 with the chemical modification), 0.3 µM of exon 2 melt probe (SEQ ID NO: 5), 0.7 µM exon 3 upstream (excess) primer (SEQ ID NO: 6), 0.1 µM exon 3 downstream (limiting) primer (SEQ ID NO: 7), 0.3 µM of exon 3 melt probe (SEQ ID NO: 8), 50 mM Tricine (pH 7.7), 57 mM potassium acetate (pH 7.5), 8% glycerol, 1% DMSO, 200 µM of each dATP, dCTP and dGTP, 400 µM dUTP, 50 µM dTTP, 0.01% Tween-20, 0.04 units/µl of uracil-N-glycosylase (UNG), 0.6 units/µl of ΔZ05 GOLD DNA polymerase and 3 mM magnesium acetate. A mixture of two limiting primers was used for exon 2: ¼ of the first primer (SEQ ID NO: 3) with an unmodified 3'-terminal cytosine, and ¾ of the second primer (SEQ ID NO: 4) with an $N^4$ benzylated 3'-terminal cytosine. This ratio of two limiting primers in the reaction allowed for optimal degree of wild-type suppression (see example 2): when the mutant DNA was absent, the wild-type DNA was amplified. However, when the mutant DNA was also present, the mutant DNA was amplified preferentially over the wild-type (data not shown).

Amplification and melt analysis were performed using the Roche LightCycler 480 instrument. The reactions were subjected to the following temperature profile: 50° C. for 5 minutes (UNG step), 95° C. for 10 minutes (polymerase activation), followed by 50 cycles of 95° C. for 10 seconds and 61° C. for 40 seconds. Fluorescence data was collected at the end of each 61° C. step to generate the growth curves (not shown). The reactions were then subjected to the melt analysis: after the last amplification cycle, the temperature was raised to 95° C. for 1 second, reduced to 40° C. for 1 minute, then increased to 95° C., while fluorescence was being measured for each 1.0° C. increase in temperature. Finally, the temperature was reduced to 40° C. to end the melt assay.

Figure 2:
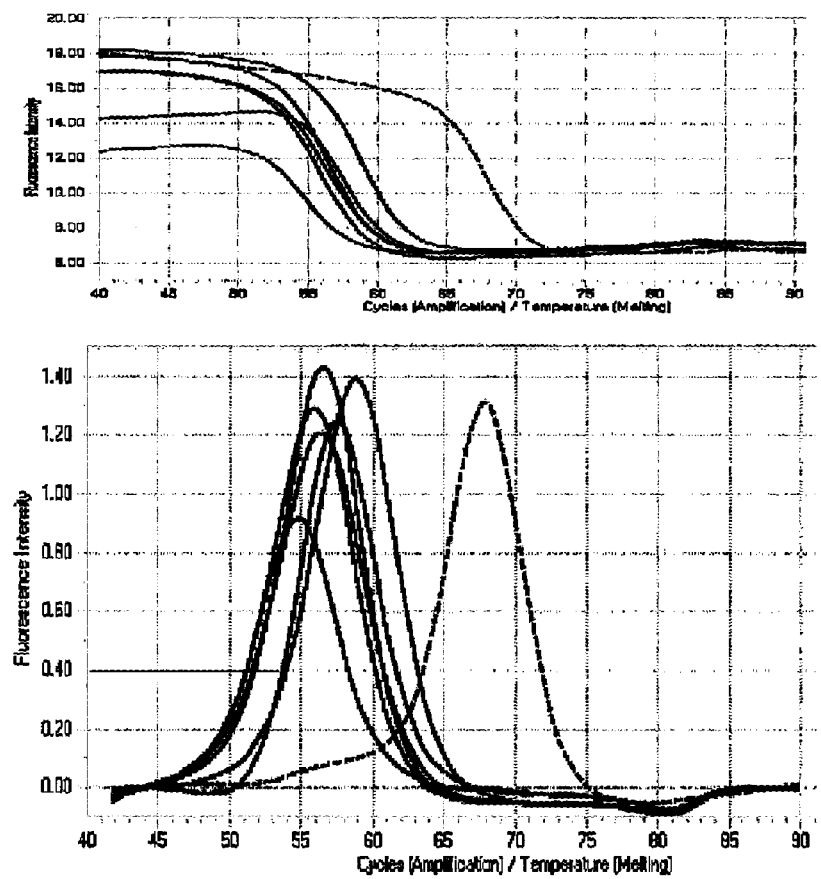
FIG. 2 shows the results of amplification and melting analysis of a wild-type and a KRAS-mutant target separately, according to Example 1 of the present invention.

The results of the melt assay are shown in FIG. 2. The raw data ("melt curves") are shown as fluorescence in the 450-500 nm wavelength interval with the change in temperature. The derivative data ("melt peaks") are shown as a first derivative (dF/dT) of the fluorescence in the same temperature interval. The mutant targets are shown as solid lines and the wild-type template is shown as a dashed line. In this example, the melt probe (SEQ ID NO: 5) emits fluorescent light of the desired wavelength when it is bound to the target nucleic acid in a duplex. With the increase in temperature, a drop in fluorescence is observed as the probe dissociates from the duplex. In the dissociated, single-stranded form, the probe assumes a conformation wherein the quencher (BHQ-2) quenches fluorescence of the fluorophore (FAM).

The results in FIG. 2 show a distinct melting profile for the mutant sequences (solid lines) and the wild-type sequence (dotted line). The mutant samples are identified by a lower melt peak maximum ($T_m$) than the wild type sample. The lower $T_m$ is due to a lower degree of complementarity between the probe and the mutant sequence. The mutant peaks show variation in $T_m$ because the samples contain different mutations in codon 12 or codon 13.

Example 2

Allele-Specific Amplification and Detection of KRAS Mutations in a Mixture of Wild-Type and Mutant Samples In this example, the amplification and melt analysis were performed on a mixture of wild type target and a mutant target in the same tube. Each 50 µl reaction contained 8,000 copies of target DNA comprising a mixture of the wild-type and mutant sequences. The mutant sequence comprised either 1% or 5% of the total copy number in the reaction, the remaining 99% or 95% being the wild-type sequence. The amplification and melt analysis were performed using the conditions and temperature profile as generally described for Example 1, with modification indicated for each particular experiment. The results are shown on FIGS. 3-8. The mutant targets are identified by a lower melt peak maximum ($T_m$) than the wild type targets. The solid lines represent "suppressive conditions", while the dashed lines represent "control conditions" specified for each experiment.

Figure 3:
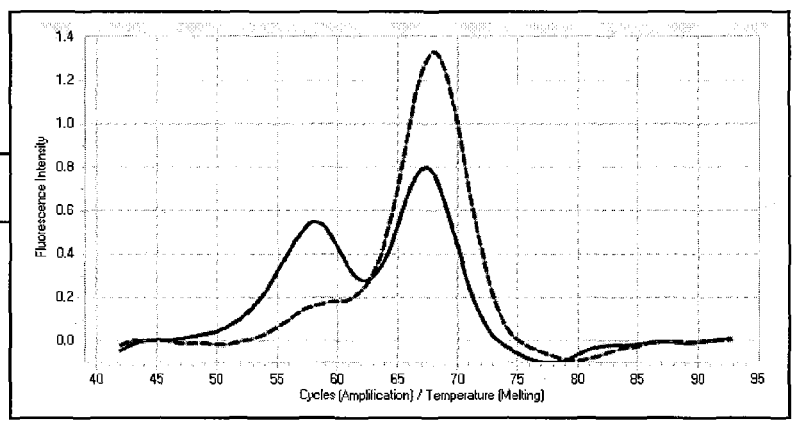
FIGS. 3-8 show the results of allele-specific amplification and detection of KRAS mutations in a mixture of wild-type and mutant samples, according to Example 2 of the present invention.
Figure 3:
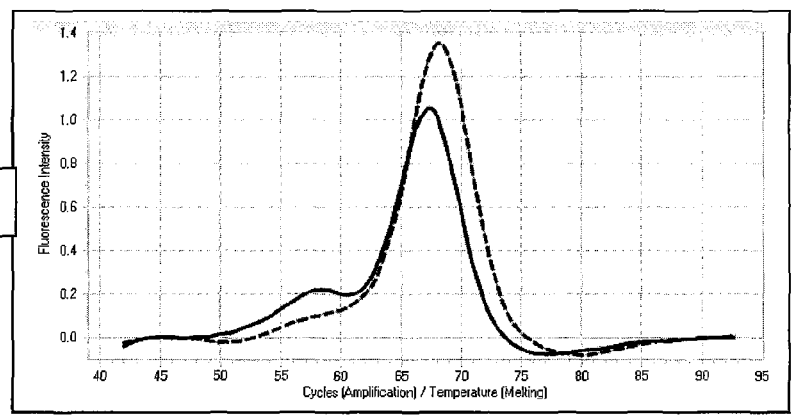

In FIG. 3, the suppressive conditions are: the limiting primer is a mixture of SEQ ID NO: 3 and 4 and the enzyme has a hot-start capability (ΔZ05 GOLD). The control conditions are: the limiting primer is only SEQ ID NO: 3 (without the 3'-terminal chemical modification) and the enzyme has no hot-start capability (ΔZ05). For the ΔZ05 enzyme, the pH was adjusted to 8.3, and the polymerase activation step was removed from the cycling profile.

Figure 4:
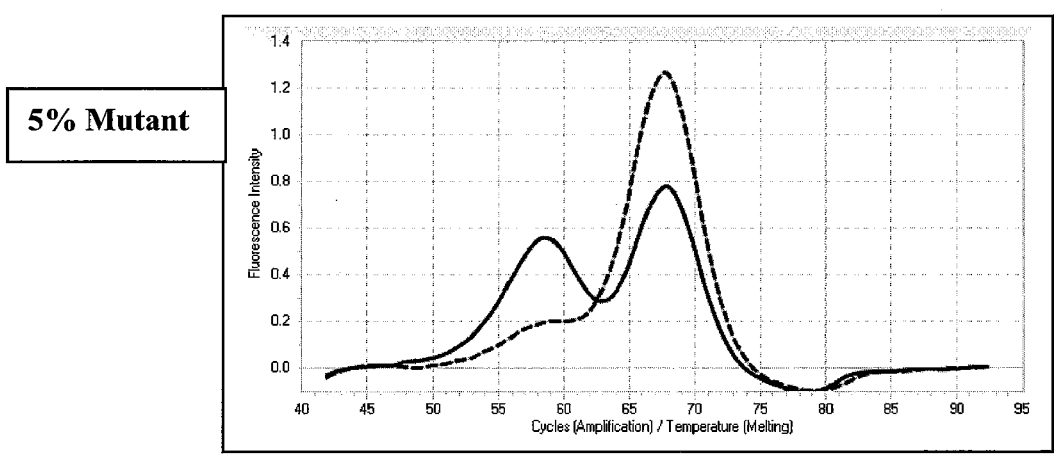
Figure 4:
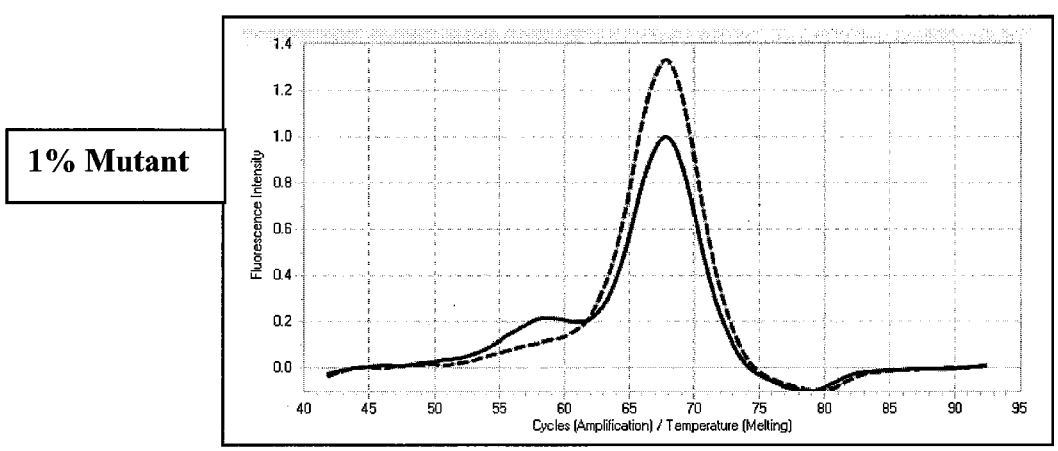

FIG. 4 shows the results of an experiment identical to that on FIG. 3, except both suppressive and control conditions employ the use of the hot-start enzyme ΔZ05 GOLD. The mixture of SEQ ID NO: 3 and 4 was used for the suppressive conditions, and SEQ ID NO: 3 only (no chemical modification) for the control conditions.

Figure 5:
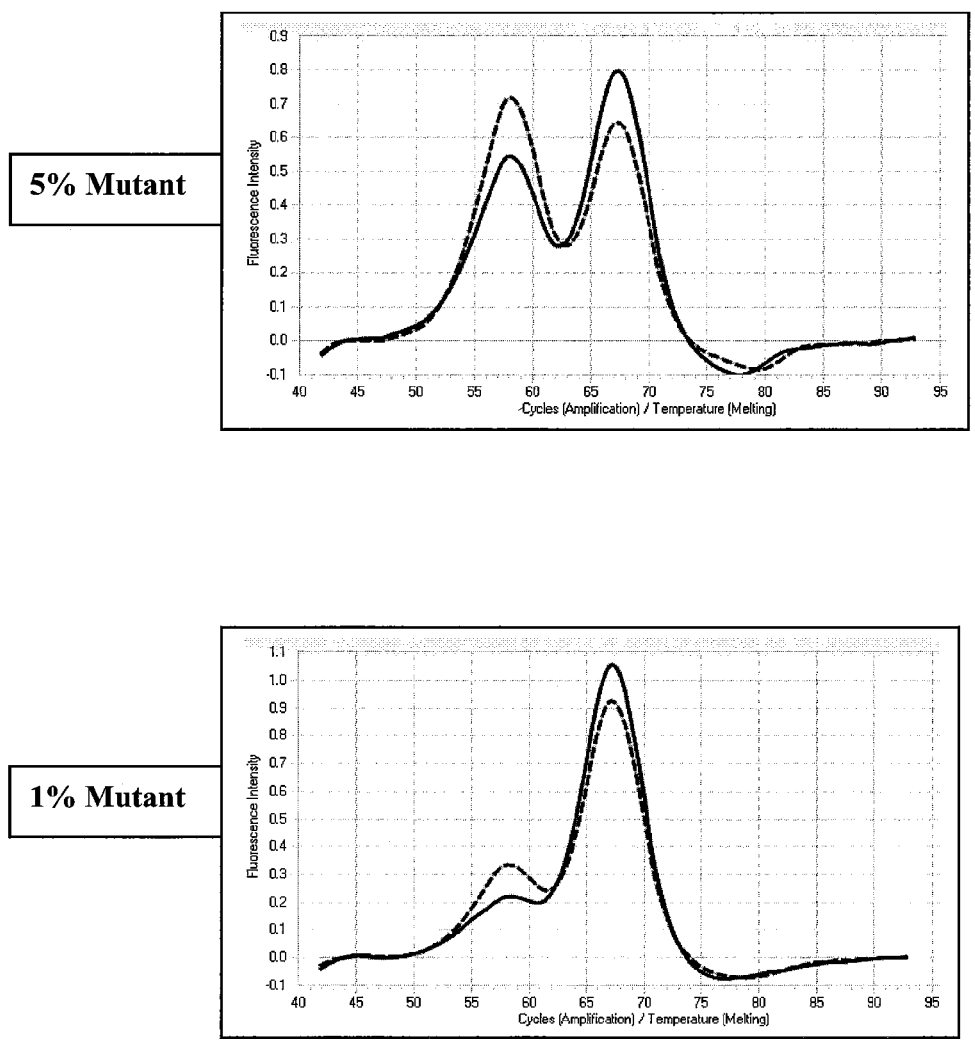

FIG. 5 shows the results of an experiment identical to that on FIG. 3, except both suppressive and control conditions employ the use of the hot-start enzyme ΔZ05 GOLD. The mixture of SEQ ID NO: 3 and 4 was used for the suppressive conditions and SEQ ID NO: 4 only (with chemical modification) was used for the control conditions. The results demonstrate that using the combination of primers tempers the amount of suppression and ensures that the wild-type sequences are amplified in the absence of the mutant sequences.

Figure 6:
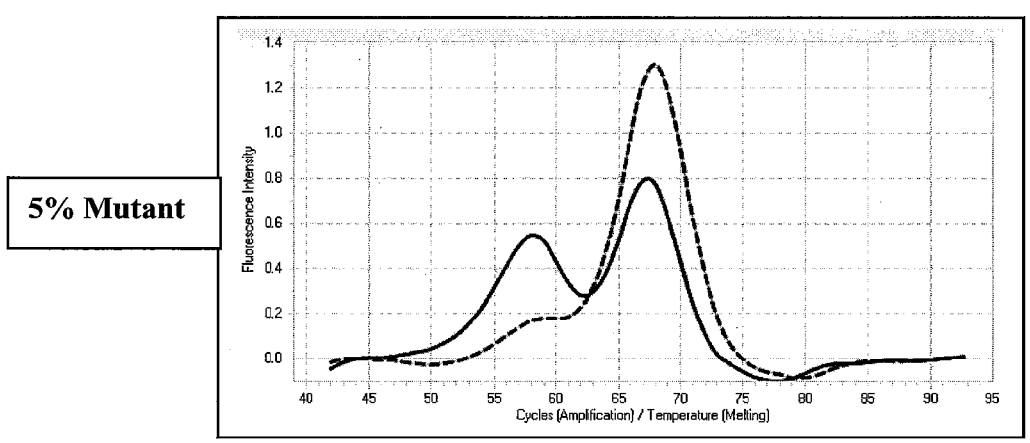
Figure 6:
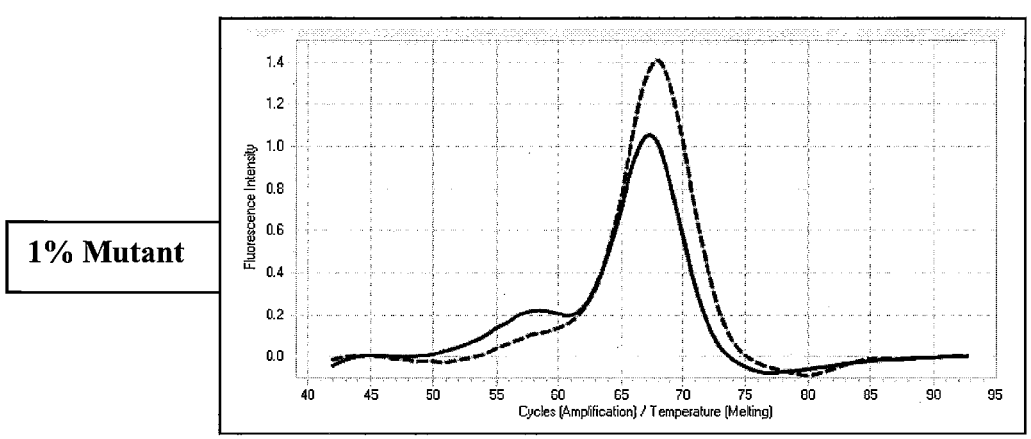

FIG. 6 shows the results of an experiment identical to that on FIG. 3, except both suppressive and control conditions employ the use of the mixture of SEQ NO: 3 and 4. The suppressive conditions use a hot-start enzyme ΔZ05 GOLD, while the control conditions use a non-hot-start enzyme ΔZ05.

Figure 7:
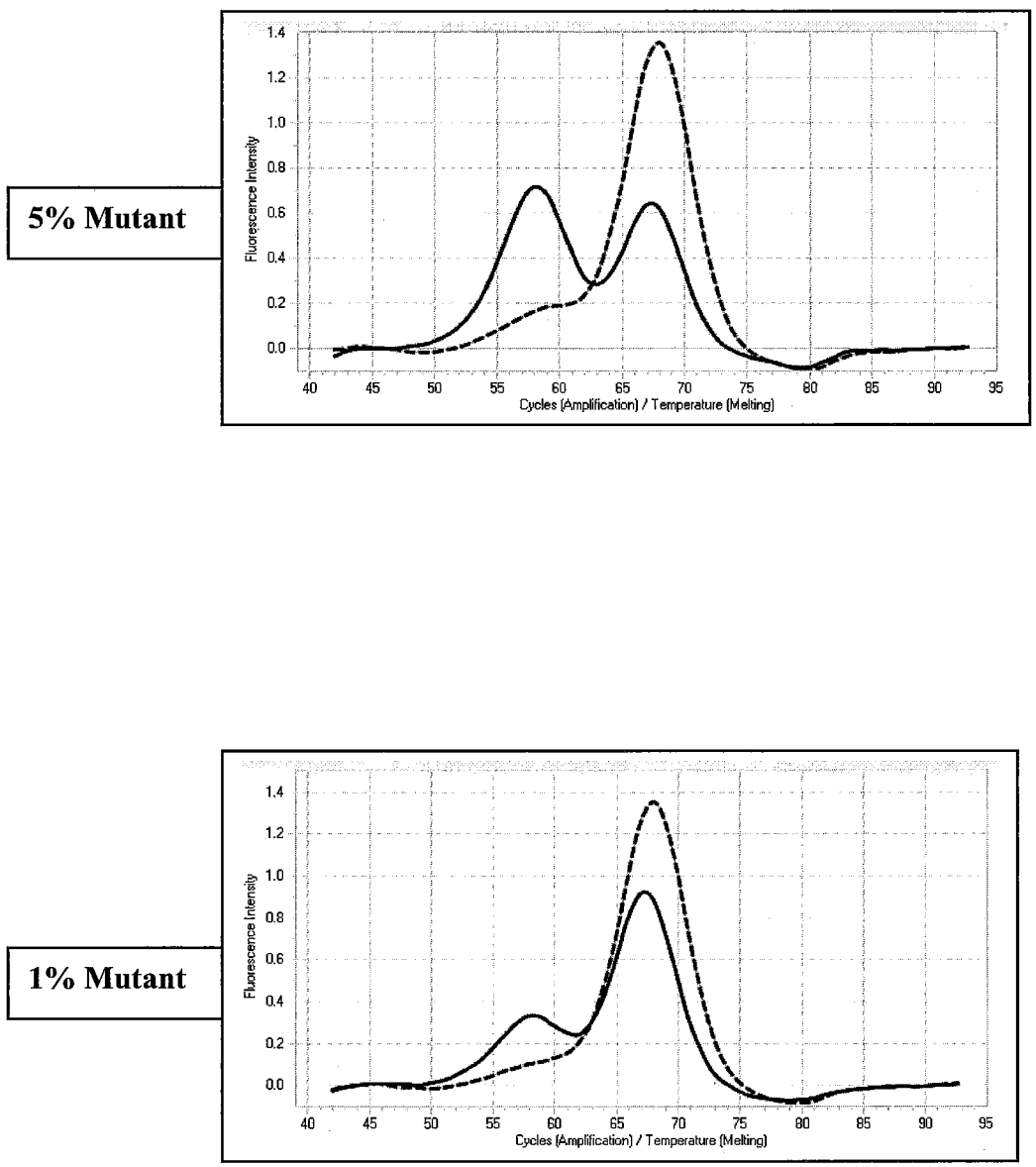

FIG. 7 shows the results of an experiment identical to that on FIG. 3, except both suppressive and control conditions employ the use of SEQ NO: 4 only (with a chemical modification). The suppressive conditions use a hot-start enzyme ΔZ05 GOLD, while the control conditions use a non-hot-start enzyme ΔZ05.

Figure 8:
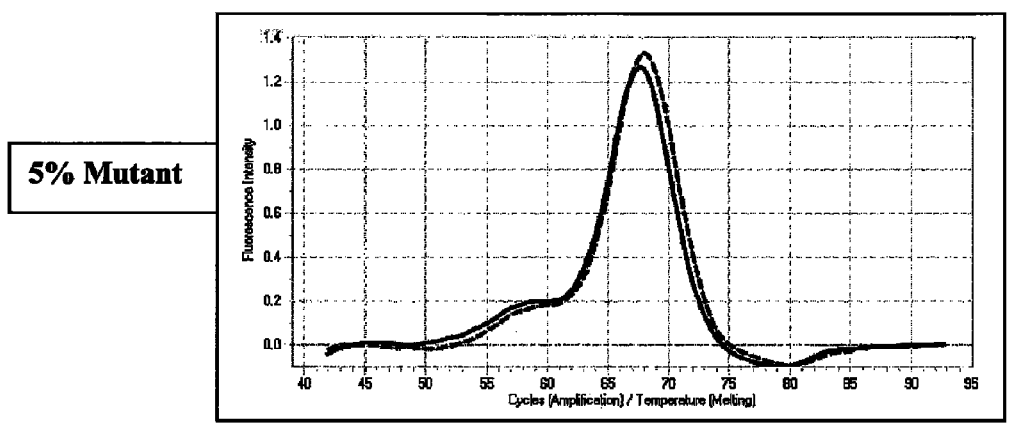
Figure 8:
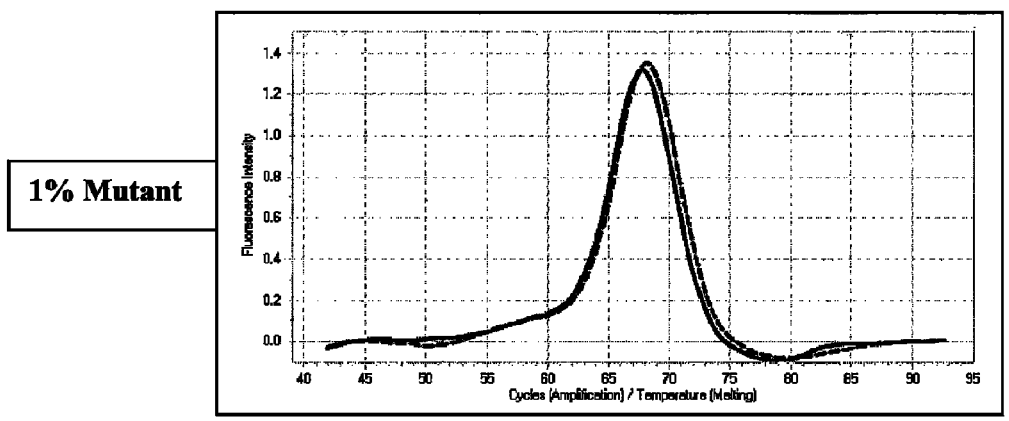

FIG. 8 shows the results of an experiment identical to that on FIG. 7, except both suppressive and control conditions employ the use of SEQ NO: 3 only (no chemical modification). As in the example illustrated on FIG. 7, the suppressive conditions use a hot-start enzyme ΔZ05 GOLD, while the control conditions use a non-hot-start enzyme ΔZ05. In this experiment, the "suppressive" conditions yielded no suppression.

The results demonstrate that suppression of wild-type amplification improves the yield of the mutant amplicon.

When the mutant sequence constitutes 1% of the total target sequence, the mutant sequence is not detectable without the wild-type suppression. At higher concentration of the mutant sequence, the yield of the mutant amplicons is also noticeably improved by the wild-type suppression.

Example 3

Allele-Specific Amplification and Detection of KRAS Mutations in Samples of Patient-Derived Formalin-Fixed Paraffin-Embedded Tissues (FFPET)

Figure 9:
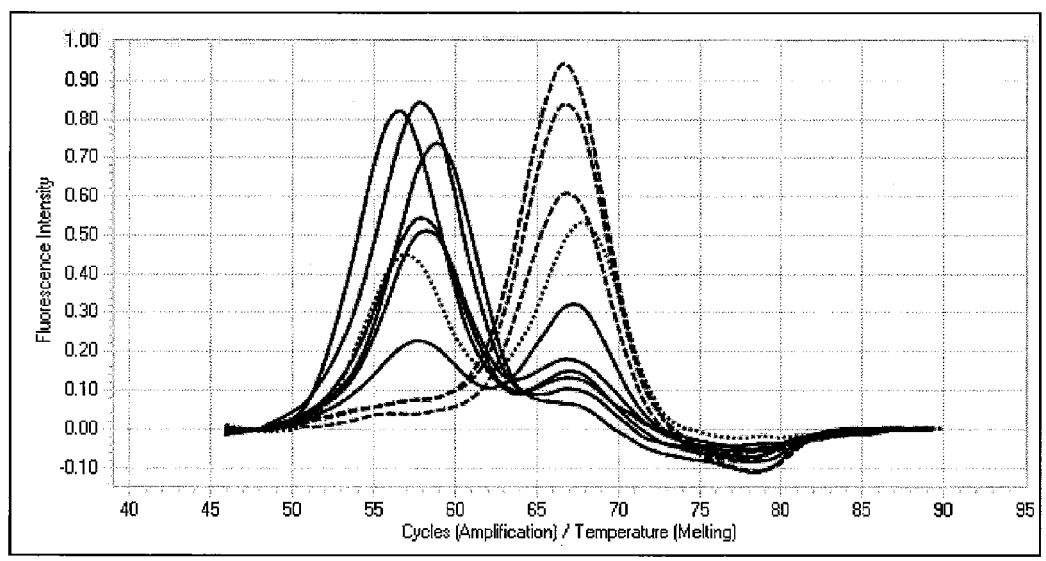
FIG. 9 shows the results of allele-specific amplification and detection of KRAS mutations in samples of patient-derived formalin-fixed paraffin-embedded tissues (FFPET), according to Example 3 of the present invention.

In this example, amplification and melt analysis were performed on DNA extracted from seven commercially obtained FFPET samples. Each 50 µl reaction contained 25 ng of FFPET DNA, extracted from 3×10 µm sections of tissue and quantified on a Nanodrop spectrophotometer. A reaction containing 5% of the mutant target mixed with 95% wild-type target was used as a control (dotted line). The amplification and melt analysis were performed using the conditions and temperature profile described in Example 1, except the exon 3 primers and probes were not present in the reaction mixture, the amount of ΔZ05 GOLD polymerase was reduced to 0.3 units/µl and magnesium acetate was reduced to 2.5 mM. The results are shown in FIG. 9 as melting peaks. The mutant targets are identified by a lower melt peak maximum ($T_m$) than the wild type targets. The dashed lines show wild-type sequences while the solid lines show patient samples where mutant sequences are present. Some patient samples contain both the wild-type and the mutant sequences.

FFPET DNA is known to be highly fragmented and difficult to amplify and detect. However, the results in FIG. 9 clearly show successful amplification and detection of the mutant DNA present in the background of the wild-type DNA in the FFPET sample. The variation among $T_m$'s of the mutant targets reflects different codon 12 or 13 mutations of the KRAS gene as verified by sequencing (data not shown).

While the invention has been described in detail with reference to specific examples, it will be apparent to one skilled in the art that various modifications can be made within the scope of this invention. Thus the scope of the invention should not be limited by any of the examples described herein, but by the claims presented below.

We claim:

1. A method of selective amplification of a desired variant of a target sequence, which target sequence exists in the form of more than one variant, the method comprising the steps of:
    a) providing a sample possibly comprising at least one variant of the target sequence in a reaction mixture;
    b) providing a first oligonucleotide, capable of hybridizing to more than one variant of the target sequence;
    c) providing a second oligonucleotide, capable of hybridizing to more than one variant of the target sequence, wherein at least a fraction of said second oligonucleotide contains a modified base in one or more nucleotides at or near the 3'-terminus;
    d) providing a third oligonucleotide, capable of hybridizing to the desired variant of the target sequence with lesser affinity than to an undesired variant of the target sequence and designed to hybridize to the same strand and between 0 and 60 nucleotides downstream of said second oligonucleotide;
    e) providing a nucleic acid polymerase substantially lacking 5'-3' nuclease activity;
    f) subjecting said reaction mixture to polymerase chain reaction, wherein said third oligonucleotide substantially inhibits extension of said second oligonucleotide by said nucleic acid polymerase when said third oligonucleotide is hybridized to the undesired variant of the target sequence, but does not substantially inhibit extension of said second oligonucleotide by said nucleic acid polymerase when said third oligonucleotide is hybridized to the desired variant of the target sequence.

2. The method of claim 1, wherein the amounts of said first and second oligonucleotides are unequal, such that the first oligonucleotide is present in excess.

3. The method of claim 1, wherein said modified base in said second oligonucleotide is modified at an exocyclic amino group.

4. The method of claim 1, wherein at least one of said first, second and third oligonucleotides is labeled.

5. The method of claim 1 further comprising detection of the amplified nucleic acid sequence.

6. The method of claim 1, wherein the first oligonucleotide is SEQ ID NO: 2.

7. The method of claim 1, wherein the second oligonucleotide is SEQ ID NO: 3.

8. The method of claim 1, wherein the third oligonucleotide is SEQ ID NO: 5.

9. The method of claim 1, wherein said nucleic acid polymerase possesses a hot-start capability.

* * * * *